(12) United States Patent
Bright

(10) Patent No.: US 11,002,133 B2
(45) Date of Patent: May 11, 2021

(54) MULTIGAS MULTISENSOR REDUNDANT MUDLOGGING SYSTEM

(71) Applicant: IBALL INSTRUMENTS LLC, Norman, OK (US)

(72) Inventor: Carl Bright, Harrah, OK (US)

(73) Assignee: IBALL INSTRUMENTS LLC, Norman, OK (US)

( * ) Notice: Subject to any disclaimer, the term of this patent is extended or adjusted under 35 U.S.C. 154(b) by 653 days.

(21) Appl. No.: 14/926,508

(22) Filed: Oct. 29, 2015

(65) Prior Publication Data
US 2017/0122101 A1 May 4, 2017

(51) Int. Cl.
| | | |
|---|---|---|
| E21B 49/08 | (2006.01) | |
| G01N 33/28 | (2006.01) | |
| G01J 3/453 | (2006.01) | |
| G01N 21/3504 | (2014.01) | |
| G01N 33/00 | (2006.01) | |
| G01J 3/02 | (2006.01) | |

(52) U.S. Cl.
CPC .......... *E21B 49/086* (2013.01); *G01J 3/027* (2013.01); *G01J 3/453* (2013.01); *G01N 21/3504* (2013.01); *G01N 33/0027* (2013.01); *G01N 33/2823* (2013.01); *E21B 49/0875* (2020.05); *G01J 2003/4534* (2013.01); *G01N 2201/0221* (2013.01)

(58) Field of Classification Search
CPC .... E21B 49/086; E21B 49/0875; G01J 3/027; G01J 3/453; G01N 21/3504; G01N 33/0027; G01N 33/2823
See application file for complete search history.

(56) References Cited

U.S. PATENT DOCUMENTS

| | | | |
|---|---|---|---|
| 2,500,213 A | 3/1950 | Stevens | |
| 5,473,162 A | 12/1995 | Busch et al. | |
| 5,801,384 A * | 9/1998 | Kirchhevel | ........ G01N 21/3504 |
| | | | 250/239 |
| 7,151,260 B2 * | 12/2006 | Markham | .......... G01N 21/3504 |
| | | | 250/339.06 |
| 8,411,262 B2 | 4/2013 | Ford et al. | |
| 8,436,296 B2 | 5/2013 | Ford et al. | |
| 8,733,803 B2 | 5/2014 | Ford et al. | |
| 8,885,163 B2 | 11/2014 | Morys et al. | |
| 8,921,768 B2 | 12/2014 | Jones et al. | |
| 8,946,660 B2 | 2/2015 | Pelletier et al. | |
| 9,010,441 B2 | 4/2015 | Tose | |

(Continued)

FOREIGN PATENT DOCUMENTS

KR 100842099 B1 * 6/2008 ............. H01F 41/00

*Primary Examiner* — David P Porta
*Assistant Examiner* — Jeremy S Valentiner
(74) *Attorney, Agent, or Firm* — Hall Estill Attorneys at Law; Tyler Mantooth

(57) ABSTRACT

A new apparatus and method within a portable Mudlogging gas detection system that determines the total amounts and various composition of an incoming mix of gases extracted from drilling fluid. The Mudlogging system consists of at least one electronic computing device, at least one infrared interferometer, and at least one other device for detecting gasses extracted from the drilling fluid. The Mudlogging system may switch from the primary gas detection means to a secondary gas detection means upon detection of a non-recoverable fault of the first gas detection means.

20 Claims, 4 Drawing Sheets

(56) References Cited

U.S. PATENT DOCUMENTS

| | | | |
|---|---|---|---|
| 2004/0015300 A1* | 1/2004 | Ganguli | C23C 16/52 |
| | | | 702/24 |
| 2005/0170520 A1* | 8/2005 | Schur | G01N 1/2273 |
| | | | 436/149 |
| 2008/0078544 A1 | 4/2008 | Christian et al. | |
| 2011/0313670 A1 | 12/2011 | DeGreeve et al. | |
| 2012/0182546 A1* | 7/2012 | Chaouki | G01N 21/3577 |
| | | | 356/73 |
| 2012/0316788 A1* | 12/2012 | Bedouet | E21B 21/08 |
| | | | 702/12 |
| 2013/0334412 A1* | 12/2013 | Gunn | G01N 33/2823 |
| | | | 250/255 |
| 2014/0208840 A1* | 7/2014 | Bright | G01N 33/0006 |
| | | | 73/152.19 |
| 2015/0053861 A1* | 2/2015 | Wong | G01N 21/3504 |
| | | | 250/343 |

\* cited by examiner

MULTIGAS MULTISENSOR REDUNDANT MUDLOGGING SYSTEM

SUMMARY

In accordance with various embodiments, a portable Mudlogging gas detection system determines the total amounts and various composition of an incoming mix of gases extracted from drilling fluid. The Mudlogging system has at least one electronic computing device, at least one infrared interferometer, and at least one other device for detecting gasses extracted from the drilling fluid.

DETAILED DESCRIPTION

Figure 1:
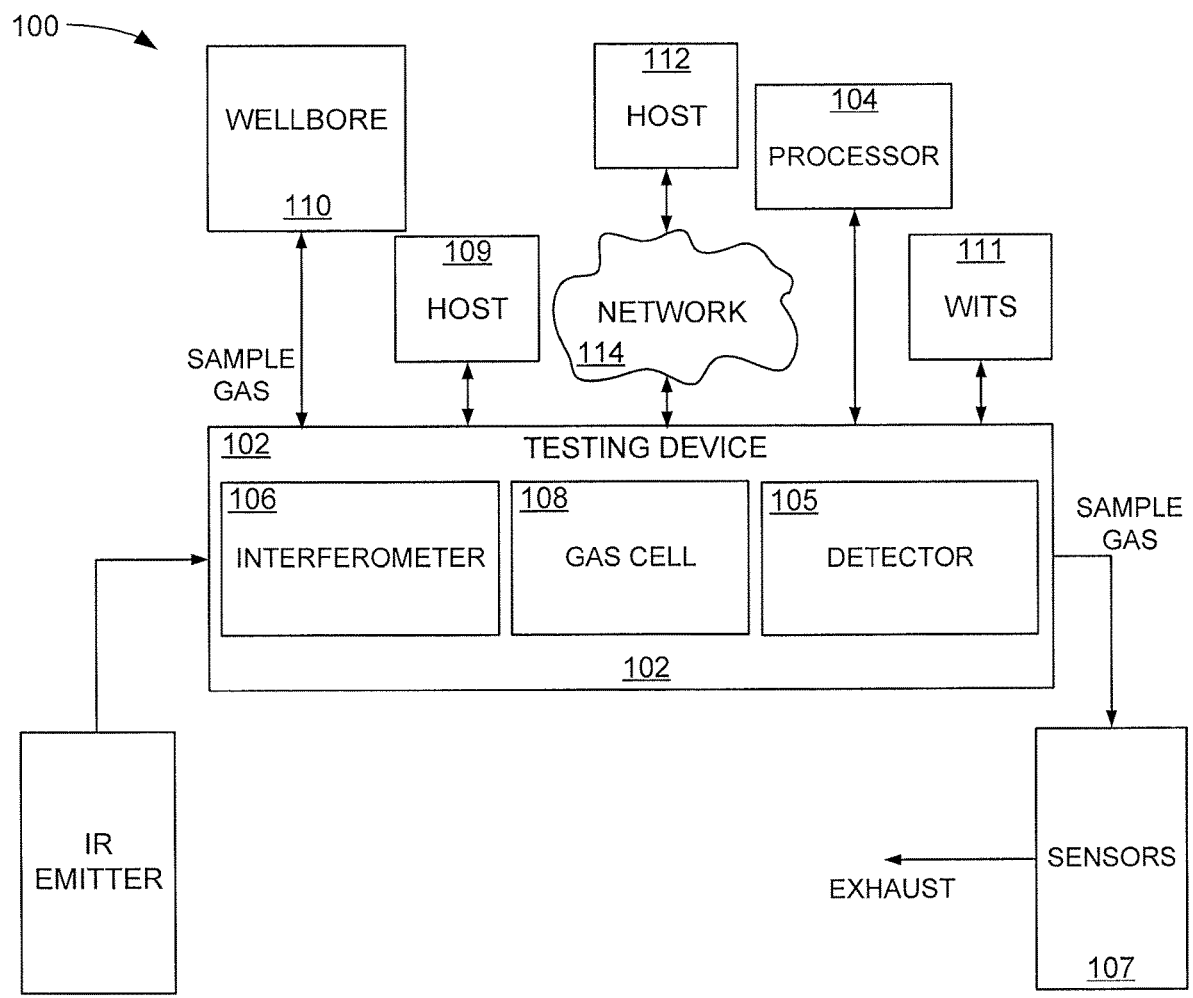
FIG. 1 represents an example hydrocarbon testing system arranged in accordance with various embodiments.

With the proliferation of more sophisticated computational devices, drilling fluid gas sample testing that traditionally was conducted in a laboratory is now performed on the well site and within the outdoor elements. This sophistication corresponds with an increase in computing power, reduced power consumption, and smaller sensors that allows a diverse variety of portable hardware and software to be employed with greater accuracy and speed than if a gas sample was tested off-site.

In the mudlogging industry where, among other things, drilling fluids are tested on-site to detect dissolved gasses within the drilling fluid during the drilling process, a computing device and gas sensing equipment can improve the reliability, speed and accuracy of the gas sample being tested. However, such on-site computers and sensing equipment most times are not fully reliable enough for the pendency of the drilling operation and they do not contain any backup or redundant detector system to maintain important functionality until it is able to be serviced. In fact, all mudlogging companies and portable gas detection equipment suppliers have on-hand and ship multiple gas detection units to the same well site due to the very likely scenario of the first gas detection unit failing during operations.

Reliability has become a much more critical factor in today's rapid drilling speed environment. In one such example, if a hydrocarbon exploration site is drilling hundreds of feet per hour using the new generation of polycrystalline diamond compact (PDC) bits and the currently available mudlogging gas detection and analyzation instrumentation is inoperable for even a small period of time, valuable and critical information about the drilling process can be forever lost.

Accordingly, assorted embodiments employ a redundancy of gas detection systems for mudlogging operations that provide accurate and quick gas measurements in the mudlogging environment over a long-term time frame with a new built-in ability to autonomously switch to a backup sample gas detector in case of failure of one or more internal sensor types.

One embodiment incorporates a redundancy of sensors that consists of a sample gas being released from drilling fluid and then passing through an inlet gas pathway by being drawn into the apparatus by a suction pump, then the pump would push the sample gas through a gas cell portion of a interferometer system with the interferometer disposed between an infrared light source and the gas cell and with the gas cell disposed between the interferometer and a detector. After the sample gas passes through the gas cell, it would continue on and react with an Oxygen sensor, continue on and react with a Hydrogen Sulphide sensor, continue on and react with an Acetylene detector, continue on and react with a wide band infrared hydrocarbon detector, continue on and react with a wide band infrared CO2 detector. Pressures would be monitored by redundant pressure sensors and temperature sensors. At the proximal end of the multiple sensors being exposed to the sample gas, a second redundant pump would push the gasses from the instrument.

In an example embodiment, the infrared light intended for the interferometer first passes through the interferometer prior to flowing through the gas cell. This proper sequencing of the infrared interferometer upstream of the gas cell allows for specific infrared wavelengths to be generated prior to irradiation into and absorption within the gas cell. This specific, but non-limiting, embodiment increases accuracy, speed, and long-term reliability of the interferometer since the gas under test in the gas cell is not exposed to the full spectrum of generated infrared light but only the light that has been processed by the interferometer.

FIG. 1 represents an example gas sample testing system 100 that is arranged in accordance with some embodiments. The testing system 100 has one or more testing devices 102 that can be operated independently via a local processor 104. Each testing device 102 can have at least one interferometer 106 and a gas cell 108. The passage of a gas sample through the gas cell 108 will produce varying amounts of infrared absorbance that is correlated with amounts of different hydrocarbons present in the gas sample using the Fast Fourier method. The output of the gas cell 108 is analyzed by the local processor 104 and detector 105. The sample gas then passes from gas cell 108 to the secondary sensors 107 which may comprise at least a wide band infrared hydrocarbon detector, a wide band infrared Carbon Dioxide detector, an Oxygen detector, and Acetylene detector, and a Hydrogen Dioxide detector.

It is noted that while a gas sample may be procured from any location and environment, assorted embodiments position a testing device 102 no greater than 100 feet from a wellbore 110. The minimal distance from the wellbore 110 to the testing system 100 mitigates damage to the sample line, entrapped gases from escaping, and entrapped gases from being diluted while traversing to and through the testing device 102. It is contemplated that the testing device 102 is configured to be portable and housed within an explosion-proof case that can be transported by a person without the use of any mechanical equipment, such as a dolly, forklift, or vehicle. Testing device 102 could also be used distally at ranges over 100 foot hazard zone and placed within a plastic enclosure.

The ability of the testing device 102 to conduct gas testing operations independently is complemented by the ability to connect to one or more remote host 112 via a wired or wireless network 114 or a local host 109. A remote host 112 or local host 109 can be a server, node, processor, or other testing device 102 that may be utilized concurrently, redundantly, or successively with a local testing device 102 to improve the accuracy, speed, and breadth of gas sample testing. For example, different testing devices 102 may employ different sensors, such as the pellistor, non-dispersive infrared (NDIR), Fourier Transform infrared (FTIR), or other infrared detectors that have overlapping wavelength absorption spectrums and can be utilized to cross-check and verify the accuracy of the respective testing devices 102 and act as a redundant sensing system in case of the failure of the primary sensing system.

Testing device 102 can also be hooked up to a local drilling rig Electronic Drilling Recorder (EDR) in which the testing device 102 can communicate via duplex communications via the Wellsite Information Transfer System (WITS) connection 111. In this connection configuration the testing device 102 can transmit and receive gas detection information with the drilling rig as well as transmit and receive other drilling rig parameters. The device processor 104 can conduct continuous, sporadic, or random measurements of the gas sample and testing environment, such as temperature, humidity, and barometric pressure, which can optimize gas sample testing by adjusting the testing conditions. For example, a detected testing environment can result in gas sample flow being adjusted.

As another non-limiting example, an encountered testing environment can trigger a testing device processor 104 to alter the generation of wavelengths to broaden, or narrow, the range of wavelengths produced. Further device process 104 can further detect the failure of one or more sensors and attempt to correct for drift or failure. Upon realizing that it is unable to adjust, correct, or repair a drift or failure may opt to autonomously switch to a secondary hydrocarbon detection means.

Figure 2:
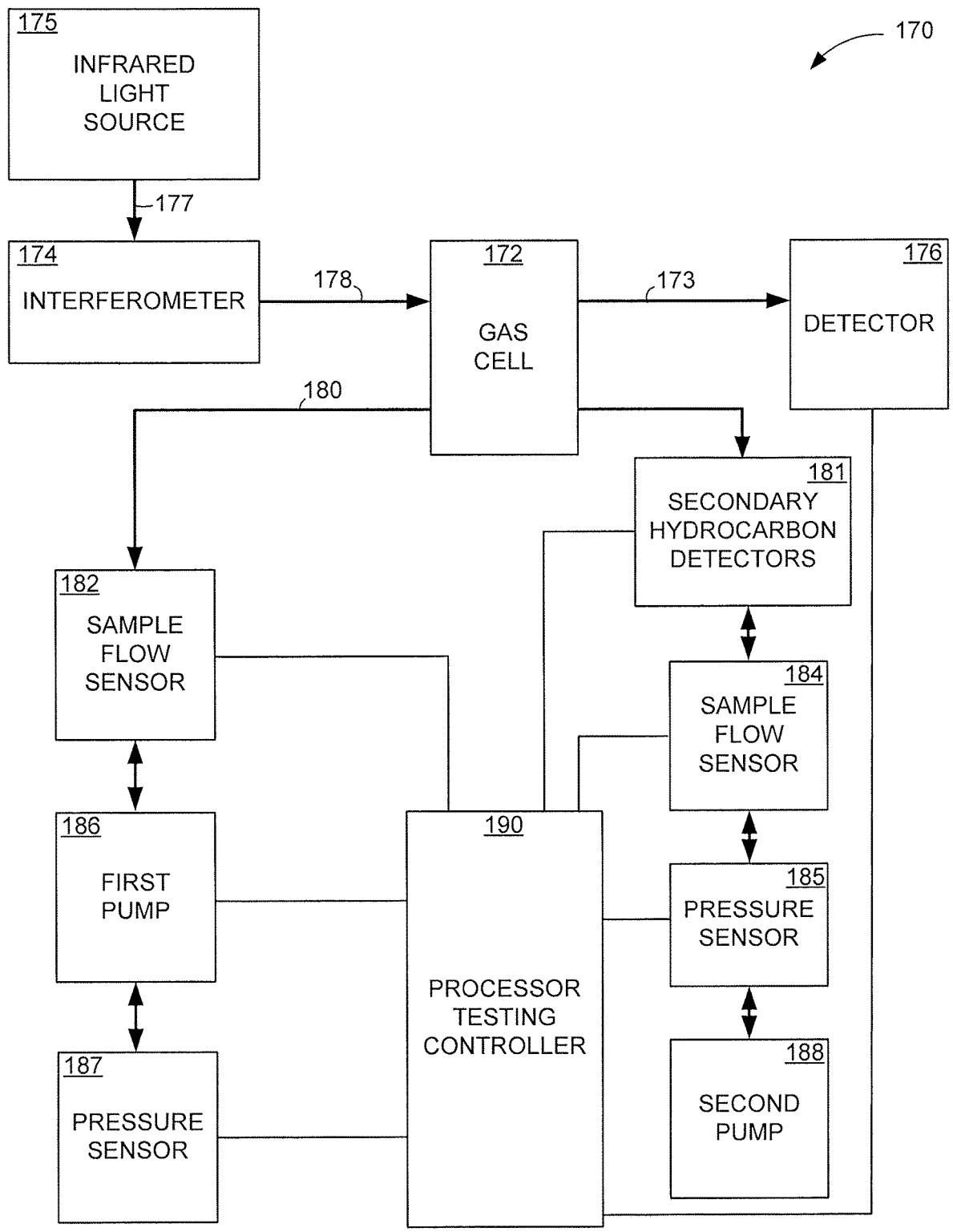
FIG. 2 displays a block representation of a portion of an example Multisensor Mudlogging System capable of being utilized in the testing system of FIG. 1.

FIG. 2 is a block representation of a portion of an example Multisensor Mudlogging System capable of being utilized in the testing system 100 of FIG. 1 in accordance with some embodiments to allow the flow of a gas sample to be customized to optimize hydrocarbon testing. An infrared generator 175 (infrared light source) generates infrared radiation and passes it to a connected interferometer 174 through a wave pathway 177 where the light is processed. A gas cell 172 is positioned between an interferometer 174 and at least one detector 176 with a wave pathway 178 extending there between. The wave pathway 178 intersects with a gas sample that travels along a sample pathway 180 through the gas cell 172. The infrared light then passes through a wave pathway 173 to one or more detectors 176.

After the gas sample passes through the gas cell 172, it then passes through the secondary hydrocarbon detector 181. The secondary hydrocarbon detector 181 may contain but not be limited to a pellistor detector, a non-dispersive infrared detector (NDIR), a Fourier Transform infrared detector (FTIR), an Oxygen detector, a Hydrogen Sulphide detector, and an Acetylene detector. Although not required, various embodiments position upstream 182 and downstream 184 gas (sample) flow sensors and pressure sensors 185 and 187 on opposite sides of the gas cell 172 and the secondary hydrocarbon detector 181 to detect environmental and operational conditions within the sample chamber encountered by a flowing gas sample.

The gas (sample) flow sensors 182 and 184 and pressure sensors 187 and 185 are respectively connected serially to first 186 and second 188 gas pumps that can be used concurrently or independently to direct gas derived from a wellbore through the gas cell 172 and secondary hydrocarbon detector 181. It is noted that the pumps 186 and 188 can flow sample gas through the gas cell 172 and secondary hydrocarbon detector 181 in opposite directions, which can allow for redundant testing as well as gas cell 172 cleaning or purging of drawn contaminates or water.

As shown, the pumps, flow sensors, and detectors are all electrically connected to a testing controller 190, which may be a local or remote controller, such as the testing device processor 104. The testing controller 190 can detect and log testing conditions, such as gas flow rate, pressures, pump efficiency, and detector latency, to allow for the real-time, automatic customization of the testing system 170 to accommodate the detected conditions. For example, the testing controller 190 may detect occluded gas sample flow in the gas cell 172 or blockage in the gas cell 172 and direct the first 186 and second 188 pumps to perform flow optimizing operations, which may involve pulsing or high-rate flow in one or more directions through the gas cell 172. As a result, gas sample flow through the gas cell 172 is assured to be clear and optimized for atomic infrared absorption that allows the detector 176 to accurately sense the presence of hydrocarbons.

Some embodiments utilize a prediction algorithm in the testing controller 190 to proactively alter gas sample flow and/or hydrocarbon detection to provide the most accurate results. As such, the testing controller 190 can change flow rates, pressure, flow direction, wavelength range, and absorption analysis to cater to the environmental and operational conditions present proximal a wellbore 110. The testing controller 190 can also switch from the primary hydrocarbon detector to the secondary hydrocarbon detector autonomously upon the detection of a fault condition. As a non-limiting example, the testing controller 190 may change from a Fabry-Perot analysis of wavelength absorption to Fourier Transform analysis or back again. As another example, the testing controller 190 may conduct different wavelength absorption analyses on a single gas flow sample to validate the accuracy of testing results.

The ability to proactively predict testing conditions based on prior logged environmental and operational conditions and results allows the testing system 170 to mitigate errors and maintain testing accuracy and speed despite changing testing conditions. Such predictive and proactive activities can be particularly advantageous in the analysis of drilling mud as vastly different volumes of hydrocarbon concentrations can quickly degrade testing accuracy and speed. For instance, the testing controller 190 can detect changing gas sample flow and/or hydrocarbon concentrations and predict that increased concentrations of heavier hydrocarbons are going to be present, which allows the gas flow to be decreased and a different infrared wavelength analysis to be proactively set to maintain testing accuracy.

Figure 3:
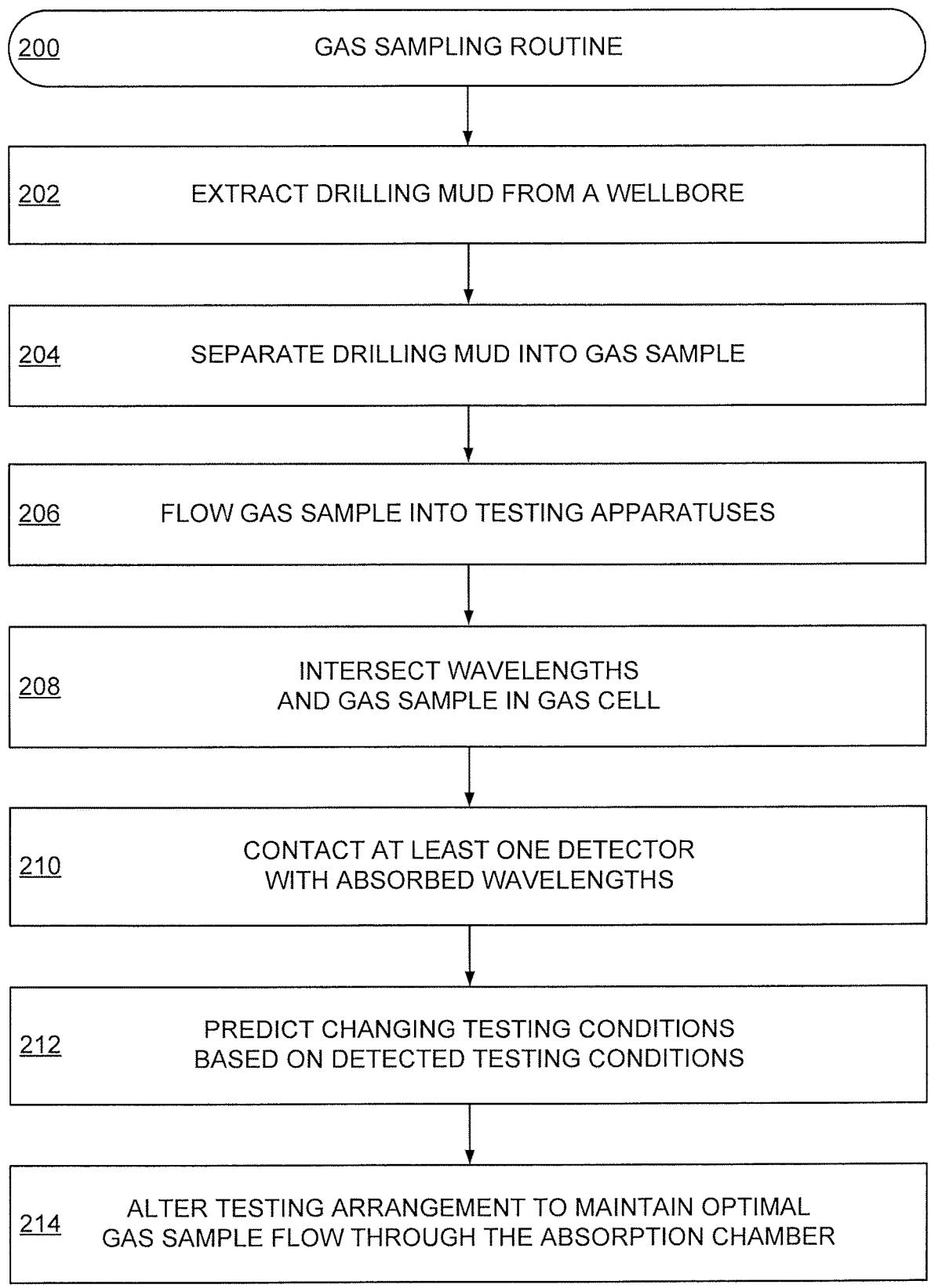
FIG. 3 is an example gas sampling routine carried out in accordance with assorted embodiments with the Multi sensor Mudlogging System of FIG. 1.

FIG. 3 provides a flowchart of an example gas sampling routine 200 that may be executed by a local and/or remote controller in accordance with various embodiments. The routine 200 begins by extracting drilling mud from a wellbore in step 202 with the mud containing hydrocarbons from one or more underground reservoirs. Step 204 then separates the drilling mud into a gas sample that flows into one or more testing apparatuses in step 206.

In step 208, the multiple different wavelengths from the interferometer and the gas sample intersect in a gas cell and the gas sample absorbs portions of the wavelengths, which shows up when the assorted wavelengths contact at least one detector in step 210 downstream from the absorption chamber. It is contemplated that steps 202 through 210 can be continuously and sporadically conducted without alteration. However, changing testing conditions, such as temperature, humidity, gas sample flow, pressure, and gas sample hydrocarbon concentrations, can trigger step 212 to predict further testing condition changes, such as future turbulent gas sample flow or decreased hydrocarbon testing accuracy, based on the comparison of detected testing conditions to previously logged testing accuracy and speed for similar testing conditions.

The prediction of degraded testing accuracy and/or speed advances routine 200 to step 214 where the testing arrangement is altered to maintain optimal gas sample flow, hydrocarbon identification accuracy, and testing speed despite new testing conditions. The ability to proactively accommodate to changing testing conditions allows routine 200 to adapt to the testing analysis type, such as FTIR, NDIR, pellistor, or other type of detector to the correct gas pressure and gas flow, such as increased, decreased, or reverse sample flow, and to optimize the speed and accuracy of hydrocarbon testing.

Figure 4:
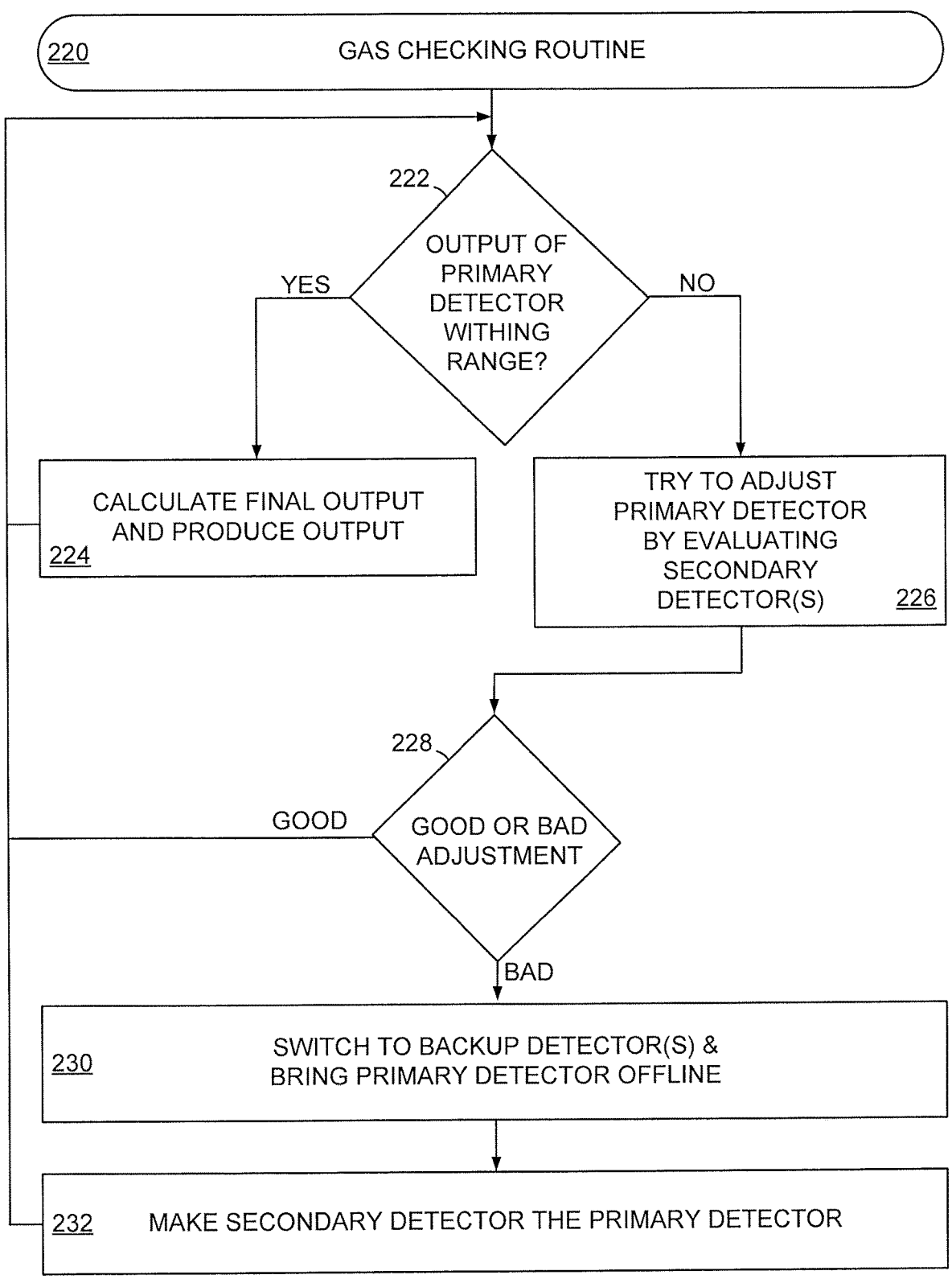
FIG. 4 provides an example gas switching routine from primary gas sample testing to secondary gas sample testing carried out in accordance with assorted embodiments with the Multisensor Mudlogging System of FIG. 2.

FIG. 4 provides a flowchart of an example gas checking routine 220 that conducts error detection, error correction, and/or switching to a backup method of hydrocarbon detection means in accordance with various embodiments. The routine 220 begins by checking the availability of the primary detector and it's ready state. Decision 222 then evaluates the output of the primary detector output and determines if it is within specified operational parameters. If the output parameters of the primary detector are optimal, then the positive state of decision 222 is achieved and step 224 calculates and subsequently produces an output before returning to decision 222.

However, if the output of the primary detector is not optimal in decision 222, routine 220 proceeds to step 226 where at least one adjustment is attempted on the primary detector in an effort to alter the detector output and compensate for the non-optimal operation so that the detector once again conforms to operational parameters. After the attempted adjustment to the primary detector is performed by step 226, the output of the primary detector is re-evaluated in decision 228. If the adjustment state of the primary detector is good according to a local or remote host, such as a local control module, the Mudlogging system then resumes normal operation by returning to decision 222. However, if the adjustment state is identified as bad according to a host, the device has the option to re-attempt an adjustment via step 226 or to pass on to step 230 where the primary detector is deactivated and switched out in favor of one or more secondary sensors. In this condition, the secondary detector(s) are set to the primary detector by a host in step 232 prior to the routine 220 returning to decision 222.

What is claimed is:

1. An apparatus comprising:
a portable case housing at least one computing device connected to a wide band infrared emitter configured to emit focused infrared light into a Fourier Transform Infrared (FTIR) interferometer;
a gas cell housed within the portable case and adapted to receive a sample gas and a processed light from the FTIR interferometer to irradiate the sample gas;
a detector positioned in the portable case to collect unabsorbed processed light from the gas cell;
a controller of the at least one computing device adapted to measure a first testing condition within the portable case and alter a second testing condition within the portable case in response to a predicted testing condition within the portable case computed by the controller based on the first testing condition measured by the controller;
at least one redundant detector positioned in the portable case and configured to detect hydrocarbons in the gas sample from the FTIR interferometer; and
at least one pump connected to the gas cell and positioned to move the gas sample from the gas cell to the detector in a first direction during the first testing condition and to the at least one redundant detector positioned in the portable case in response to the predicted testing condition, the at least one pump moving the gas sample in a second direction in response to one or more detected contaminants, the second direction being reverse of the first direction.

2. The apparatus of claim 1, wherein the apparatus is positioned within 100 feet of a wellbore.

3. The apparatus of claim 1, wherein the apparatus is housed in a portable explosion proof case.

4. The apparatus of claim 1, wherein the apparatus is housed in a portable plastic housing.

5. The apparatus of claim 1, wherein the apparatus also contains at least one radio transmitter and receiver.

6. The apparatus of claim 1, wherein the apparatus also contains external wiring connections to connect to and communicate in duplex to an external data source.

7. The apparatus of claim 1, wherein the apparatus communicates to a secondary dedicated external interface device for monitoring and control of the apparatus.

8. The apparatus of claim 1, wherein the at least one pump alters a flow of the sample gas in response to detection of an obstruction to remove the obstruction.

9. The apparatus of claim 1, wherein the at least one computing device reverses the flow of the sample gas from the first direction to the second direction via a first pump of the at least one pump and a second pump of the at least one pump to expel the one or more detected contaminants.

10. An apparatus comprising:
a portable case housing at least one computing device, a wide band infrared emitter, a Fourier Transform Infrared (FTIR) interferometer, a gas cell, a primary detector, a sample pump, and a redundant pump, the at least one computing device configured to analyze the composition of hydrocarbon gasses released from a drilling fluid, the wide band infrared emitter positioned to emit a focused infrared light into the FTIR interferometer, the FTIR interferometer positioned to emit a processed light into the gas cell to test a sample gas by irradiating the sample gas with the processed light, the primary detector positioned to collect an unabsorbed light from the gas cell, the sample pump positioned to selectively pass the sample gas to a first secondary detector in a first direction, a second secondary detector, a third secondary detector, and a fourth secondary detector within the portable case, the redundant pump positioned to push sample gas from the assorted secondary detectors, the primary, first, second, third, and fourth secondary detectors being different, a controller of the at least one computing device adapted to measure a first testing condition within the portable case and activate at least one secondary detector in response to a predicted testing condition within the portable case computed by the controller based on the first testing condition measured by the controller, the sample pump and redundant pump respectively moving the gas sample in a second direction from within the portable case in response to a detected contaminant, the first and second directions being opposite.

11. The apparatus of claim 10, wherein the apparatus also contains external wiring connections to connect to an external data Well Information Transfer System (WITS).

12. The apparatus of claim 10, wherein the apparatus also contains external wiring connections to connect to an external computer network.

13. The apparatus of claim 10, wherein the apparatus communicates wirelessly to a secondary dedicated external remote interface device for monitoring and control of the apparatus.

14. The apparatus in claim 10, wherein the system is able to compensate for internal temperatures by the use of the metal apparatus case as a heat sink.

15. A method comprising:
analyzing a composition of hydrocarbon gases released from drilling fluids within a portable case as directed by a controller of a computing device;
measuring a first testing condition within the portable case during the analyzing step as directed by the controller;
predicting a future testing condition within the portable case with the controller in response to the measured first testing condition;
altering a second testing condition within the portable case to prevent the future testing condition;
detecting a fault condition in a primary detector used to analyze the composition of hydrocarbon gases;
attempting to autonomously adjust the primary detector with the controller to correct the fault condition;
reversing flow of a gas sample within the portable case from a first direction to a second direction with at least one pump in response to a detected contaminant;
recognizing a failure to autonomously correct the fault condition;
flowing a sample gas through a gas cell of the portable case in the first direction with a first pump of the at least one pump;
passing the sample gas through a backup hydrocarbon detector in the second direction with a second pump of the at least one pump;
switching analysis of the composition of hydrocarbon gases to the backup hydrocarbon detector to compensate for the fault condition, the backup hydrocarbon detector is different than the primary detector.

16. The method in claim 15, wherein the primary detector is an interferometer and the controller and the backup hydrocarbon detector is a wide band infrared hydrocarbon detector.

17. The method in claim 15, wherein the primary detector is a wide band infrared hydrocarbon detector and the controller identifies an inaccuracy in the primary detector prior to deactivating, adjusting, and/or compensating the wide band infrared hydrocarbon detector autonomously with an at least one sensor.

18. The method in claim 15, wherein the primary detector is an internal oxygen sensor and the controller identifies an inaccuracy in the primary detector prior to deactivating, adjusting, and/or compensating the oxygen sensor autonomously with an at least one sensor.

19. The method in claim 15, wherein the primary detector is an internal Acetylene detector and the controller identifies an inaccuracy prior to deactivating, adjusting, and/or compensating the Carbon Dioxide sensor autonomously with an at least one sensor.

20. The method of claim 15, wherein the autonomous adjustment of the primary detector deactivates and subsequently reactivates the primary detector.

* * * * *